US008070766B2

(12) United States Patent (10) Patent No.: US 8,070,766 B2
Nicholls et al. (45) Date of Patent: Dec. 6, 2011

(54) SKIN PRICKING APPARATUS

(75) Inventors: Clive Nicholls, Stokenchurch (GB); Jeremy Marshall, Oxford (GB)

(73) Assignee: Owen Mumford Limited, Oxfordshire (GB)

( * ) Notice: Subject to any disclaimer, the term of this patent is extended or adjusted under 35 U.S.C. 154(b) by 56 days.

(21) Appl. No.: 11/792,848

(22) PCT Filed: Dec. 19, 2005

(86) PCT No.: PCT/EP2005/056923
§ 371 (c)(1), (2), (4) Date: Jun. 12, 2007

(87) PCT Pub. No.: WO2006/067119
PCT Pub. Date: Jun. 29, 2006

(65) Prior Publication Data
US 2008/0077168 A1 Mar. 27, 2008

(30) Foreign Application Priority Data
Dec. 21, 2004 (GB) .................................. 0427891.7

(51) Int. Cl.
*A61B 17/32* (2006.01)
(52) U.S. Cl. ...................................... 606/182
(58) Field of Classification Search .................. 606/181, 606/182, 183, 184, 185; 600/583
See application file for complete search history.

(56) References Cited

U.S. PATENT DOCUMENTS

| 4,449,529 A | 5/1984 | Burns et al. | |
|---|---|---|---|
| 4,577,630 A * | 3/1986 | Nitzsche et al. | 606/182 |
| 5,478,316 A * | 12/1995 | Bitdinger et al. | 604/135 |
| 6,136,013 A | 10/2000 | Marshall et al. | |
| 6,149,608 A | 11/2000 | Marshall et al. | |
| 6,299,626 B1 | 10/2001 | Viranyi | |
| 6,918,918 B1 * | 7/2005 | Schraga | 606/182 |
| 2002/0177787 A1 | 11/2002 | Duchon et al. | |
| 2003/0171717 A1 * | 9/2003 | Farrugia et al. | 604/131 |
| 2004/0039303 A1 | 2/2004 | Wurster et al. | |
| 2004/0215224 A1 * | 10/2004 | Sakata et al. | 606/181 |
| 2006/0173379 A1 * | 8/2006 | Rasch-Menges et al. | 600/583 |
| 2006/0264830 A1 * | 11/2006 | Hommann | 604/136 |
| 2008/0262387 A1 * | 10/2008 | List et al. | 600/583 |

FOREIGN PATENT DOCUMENTS

| EP | 0 750 881 A1 | 1/1997 |
|---|---|---|
| EP | 1 247 489 A1 | 10/2002 |
| EP | 1 362 551 A1 | 11/2003 |
| JP | 62137295 A | 6/1987 |
| JP | 64042010 U | 3/1989 |
| JP | 2002219114 A | 8/2002 |

OTHER PUBLICATIONS

Japanese Office Action, dated May 17, 2011, in Application No. 546082/2007.

* cited by examiner

*Primary Examiner* — S. Thomas Hughes
*Assistant Examiner* — Thomas McEvoy
(74) *Attorney, Agent, or Firm* — Young & Thompson

(57) ABSTRACT

A skin pricking apparatus includes a casing 1, a lancet 19 located within the casing, and a firing mechanism 5,13,31 for causing a needle tip 22 of the lancet 19 to be driven through an opening 14 in the casing to prick the skin of a user. The firing mechanism including a mechanical interlock 6,27 which is released by substantially simultaneous external pressure applied separately to two spaced apart components 5,13 of the firing mechanism by a user.

16 Claims, 2 Drawing Sheets

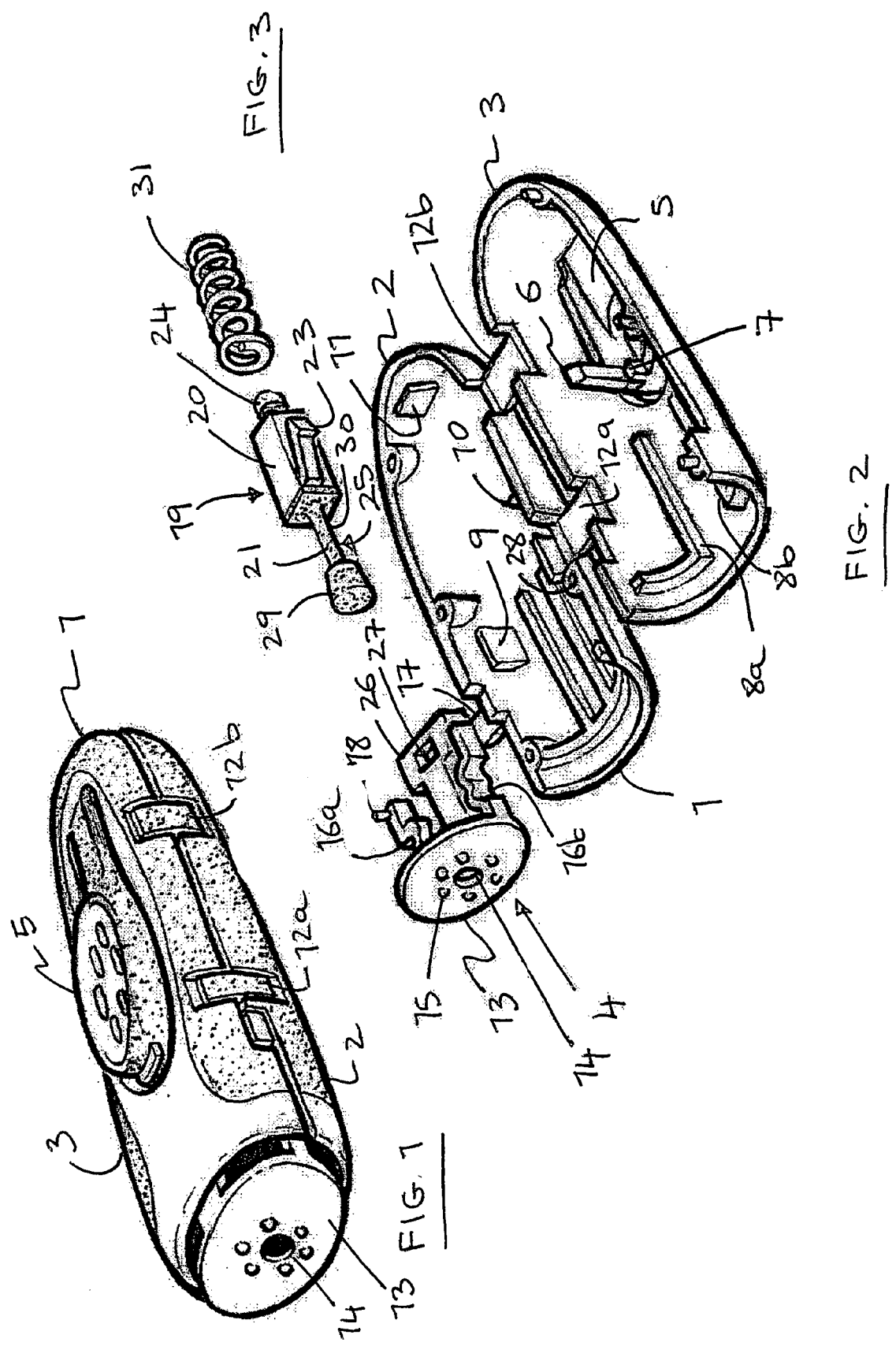

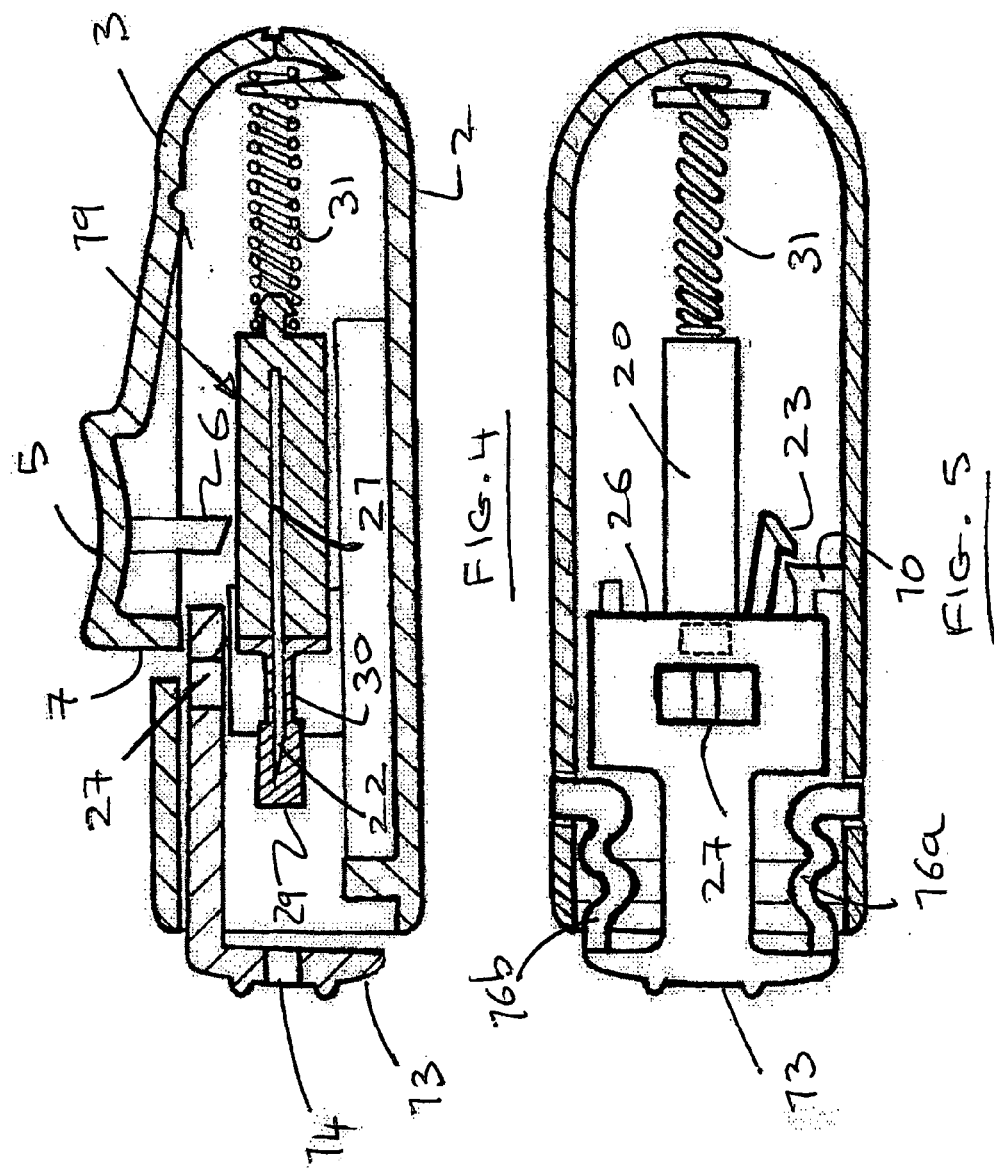

SKIN PRICKING APPARATUS

FIELD OF THE INVENTION

The present invention relates to skin pricking apparatus and in particular, though not necessarily to a skin pricking apparatus for use in providing a sample of blood.

BACKGROUND

In the medical and related diagnostic and testing fields, it is often required to take small samples of blood from a subject for the purpose of testing or analysing the blood. A common way of achieving this is by using a small needle to pierce the skin at a location where blood vessels are close to the surface. The combination of a needle and its holder is commonly known as a lancet. In order to avoid infection and contamination, lancets are preferably intended for single use and are disposable. They must therefore be compact to allow users to carry multiple lancets on their person, and cheap to manufacture.

A number of disposable lancet devices are currently on the market. These include the Unistic™ manufactured and marketed by Owen Mumford Ltd (Woodstock, UK). The current designs comprise a moulded plastics casing within which is mounted a short, spring-loaded needle. A trigger is formed in the casing which, when depressed, releases the lancet causing the tip to be fired out through an opening in the casing. Some of the current designs require a user to preload or cock the spring prior to firing. In other designs, the lancet devices are supplied already cocked. It is also generally necessary for users to remove a cap from the front of the device or the needle tip prior to firing. Users must therefore perform at least two steps, and sometimes three, in order to perform the blood sampling procedure.

There exists a desire for a lancet device or apparatus which is simpler to operate than current designs. Of course, any improved design must meet high standards with regard to manufacturing costs. It must also be reliable, ensuring that lancet devices are provided to users in an operable condition.

SUMMARY OF THE INVENTION

According to a first aspect of the present invention there is provided a skin pricking apparatus comprising a casing, a lancet located within the casing, and a firing mechanism for causing a needle tip of the lancet to be driven through an opening in the casing to prick the skin of a user, the firing mechanism comprising a mechanical interlock which is released by substantially simultaneous external pressure applied separately to two spaced apart components of the firing mechanism by a user.

Embodiments of the invention have the advantage that accidental firing of the apparatus is at the very least extremely unlikely, given that pressure must be applied to the apparatus simultaneously at two different locations. Nonetheless, firing is essentially a one-step process.

Preferably, the firing mechanism comprises:
force applying means for applying a force to the lancet to drive the needle tip through said opening;
a finger actuable trigger for coupling to said force applying means to activate that means; and
trigger locking means moveable between a first position in which coupling of the trigger to the force applying means is precluded and a second position in which coupling is allowed.

Preferably, said finger actuable trigger and said trigger locking means are molded integrally with said casing.

Preferably, said trigger and said trigger locking means are arranged to be movable in substantially mutually perpendicular directions. More preferably, said trigger locking means is moveable in a direction substantially parallel to the direction of travel of the lancet through the casing.

Preferably, the trigger locking means comprises a contact plate through which said opening is formed, the contact plate having an outer contact surface for engaging an area of a user's skin to be pricked. More preferably, the contact plate is coupled to the casing by one or more spring means arranged to bias the contact plate outwardly with respect to the casing. At least one such spring means may be attached to the casing by a flexible hinge, whereby during assembly the trigger locking means can be folded inside the casing. An advantage of this particular arrangement is that the user must apply the lancet device to the skin with a particular force in order to ensure sufficient movement of the contact plate. This is desirable as it makes it unlikely that the user will flinch sufficiently during firing to prevent a successful skin prick.

Preferably, the finger actuable trigger comprises a stop member arranged to engage a surface of the trigger locking means when the locking means is in said first position, and is arranged to be co-located with a passage through the trigger locking means when the trigger locking means is in said second position.

Preferably, said force applying means comprises a compressed spring, coupled between the lancet and the casing. The firing mechanism comprises a latch formed on the lancet or on the inside of the casing which engages a catch formed on the other of the lancet or casing. A lancet release member depends from the firing button to engage the catch or lancet when the trigger locking means is in said second position.

According to a second aspect of the present invention there is provided a skin pricking apparatus comprising a casing, a needle located within the casing, and a lancet firing mechanism, the firing mechanism comprising:
force applying means for applying a force to the needle to drive the needle through an opening in the casing to prick the skin of a user;
a finger actuable trigger for releasing the force applying means;
a trigger lock comprising a contact area for contacting a region of a users skin which is to be pricked, the lock being moveable by pressure applied to the contact area between a trigger locking position and a trigger release position According to a third aspect of the present invention there is provided a lancet for pricking a user's skin, the lancet comprising:
a body of a substantially rigid plastics material;
a needle having one end embedded in said body, leaving the other end including a sharpened needle tip to protrude from the body; and
a flexible plastics cover covering the entire exposed length of the needle, the cover being formed of such material and with such dimensions that an axial force applied to the cover relative to the body causes at least an axial portion of the cover to concertina along the needle, thereby exposing the needle tip.

Preferably, the cover is formed of such material and with such dimensions that it does not recover to cover the needle tip following removal of said axial force.

Preferably, the flexible plastics cover comprises a head portion surrounding the needle tip and a sleeve portion which is narrower than the head portion, surrounding the remainder of the needle, whereby in use said axial force is applied to the head of the cover and the sleeve portion concertinas along the needle in response.

Preferably, said flexible plastics cover is of a thermoplastic elastomer material.

Preferably, an overmolding process is used to provide said flexible plastics cover.

The lancet of the third aspect of the invention may be used in a single use skin pricking apparatus. Multiple such lancets may be used in a multi-use device, e.g. where the lancets are mounted on a revolving carousel.

According to a fourth aspect of the present invention there is provided a method of manufacturing the lancet of the above third aspect of the present invention, the method comprising forming said flexible plastics cover by overmolding a flexible plastics material on top of the needle.

According to a fifth aspect of the present invention there is provided a method of manufacturing a skin pricking apparatus, the method comprising:

- molding a single plastics component comprising upper and lower casing sections coupled together by at least one hinge, and a trigger locking section coupled to one of the upper and lower casing sections by at least one hinge;
- locating a lancet comprising a lancet needle, within one of the upper and lower casing sections, and locating spring means between the lancet and the casing; and
- folding the trigger locking section about its hinge(s) into one of the upper and lower casing sections, and folding the casing sections together about their hinge(s) to close the casing around the lancet and the spring means.

DESCRIPTION OF THE DRAWINGS

For a better understanding of the present invention and in order to show how the same may be carried into effect reference will now be made by way of example to the accompanying drawings in which:

FIG. 1 is a perspective view of a single use lancet device;

FIG. 2 is a perspective view of a moulded component used to form a casing of the lancet device of FIG. 1;

FIG. 3 is a perspective view of a lancet and spring driver of the lancet device of FIG. 1;

FIG. 4 shows a cross-section through the lancet device of FIG. 1 in a vertical plane; and FIG. 5 shows a cross-section through the lancet device of FIG. 1 in a horizontal plane.

DETAILED DESCRIPTION OF THE INVENTION

There is illustrated in FIG. 1 an assembled single use lancet device designed for pricking a users skin to provide a small blood sample. Typically a user pricks the pad of his or her finger, leaving a small spot of blood on the finger. This spot can then be collected, e.g. using a test strip, for use in performing some measurement or test. The lancet device of FIG. 1 is assembled from three separate components. These are illustrated in FIGS. 2 and 3.

FIG. 2 illustrates a casing 1 which is formed as a single moulded component. The casing is shown opened out, and has a lower casing section 2, an upper casing section 3, and a trigger locking section 4. Considering first the upper casing section 3, this comprises a trigger button 5 which is free on three sides but which is integral with the body of the casing on a fourth side, i.e. the rearmost side. The trigger is able to flex at the point of attachment to the casing body so that it can be pressed downward (as viewed in FIG. 1) by finger pressure. Depending from the lower surface of the trigger (again as viewed in FIG. 1) are a lancet release member 6 and a trigger stop member 7. The lancet release member 6 is significantly longer than the trigger stop member 7.

Two ribs 8a, 8b formed on the inside surface of the upper casing section 3 together form a lancet guide track.

Considering now the lower casing section 3, this provides on its inner surface a pair of trigger release guides 9 (only one of which is shown in FIG. 2, with the other being symmetrically located on the other side of the lower casing), a lancet catch 10, and a spring retainer member 11. The lower casing section 2 is attached to the upper casing section 3 by a pair of flexible hinges 12a, 12b.

The trigger locking section 4 of the upper casing section 3 comprises a front skin contact area or plate 13. This has an opening 14 provided therein to allow for passage of the needle tip. A number of pips 15 are disposed around the central opening 14 and are designed to create a tactile sensation upon contact with the skin which distracts the user from the actual skin pricking act. Projecting inwardly from the contact plate 13 are a pair of moulded platform "springs" 16a, 16b. A first of these springs 16a is attached at its innermost end to a flexible hinge 17 which connects the locking section 4 to the lower casing section 2. The innermost end of the other platform spring 16b is provided with a pillar 18 which engages a corresponding hole 28 formed in the lower casing section when the casing sections are folded together. A central blocking structure 26 extends inwardly from the contact plate, with a trigger release hole 27 extending through an end thereof.

FIG. 3 illustrates a lancet 19 which comprises a plastics body 20 of generally cuboid shape. The end of a needle 21 (see FIGS. 4 and 5) is embedded in the body 20, leaving the sharpened tip 22 of the needle to project outwardly from the body. Moulded integrally with the body 20 are a flexible latch 23 and a spring retaining knob 24. The exposed portion of the needle 21 including the tip 22 is overmolded with a flexible and elastic plastics cover 25, e.g. of thermoplastic elastomer (TPE) such as SANTOPRENE or EVOPRENE (alternatively, the material may be polyurethane or polyurethane foam, silicon rubber, or liquid silicon rubber). This cover 25 has an enlarged, generally frustoconical shaped, head 29, which covers the tip of the needle. The overmolding narrows in a stepwise manner to provide a narrow sleeve 30 which covers the remainder of the needle. The overmolding also covers the end surface of the body 20. The overmolding ensures sterility of the needle prior to use. Also illustrated in FIG. 3 is a steel coil spring 31 which, in the assembled device, engages the knob 24.

The casing 1 comprises a number of components which mate together once the casing is folded, and which allow the various components of the lancet to be secured in place. These are apparent from the Figures, but will not be explained in any further detail as their construction and function will be readily apparent to the person of skill in the art.

The lancet is assembled by locating the lancet 19 within the lower casing section 2, and locating the spring 31 between the knob 24 and the spring retainer member 11. The spring 31 is compressed, such that the end of the latch 23 on the body 20 flexes inwardly to allow the latch to pass over the lancet catch 10. The latch 23 then springs back to engage the catch 10, locking the lancet 19 in place. The three components of the casing are then folded together and locked in place. It is noted that once assembled, the trigger locking section 4 is supported by the trigger release guides 9, preventing downward deflection of the locking section.

Operation of the lancet device will now be described with reference to FIGS. 4 and 5, which show the lancet device in the ready-to-use configuration. In this configuration, the firing button 5 is in its resting position, with the lowermost end of the lancet release member 6 sitting above, but not in contact with, the latch 23 of the lancet. The front plate of the trigger locking section 4 is not experiencing any externally applied pressure, and as such the platform springs 16a,16b are fully extended, i.e. the trigger locking section is in an extended position. In this position, the wall of the blocking structure 26 of the trigger locking section is directly beneath the trigger stop member 7. This wall is engaged by the trigger stop member in the event that a user exerts any downward force on the trigger button, preventing engagement of the latch 23 by the lancet release member.

In order to operate the lancet, a user holds the lancet device in one hand, with his or her thumb placed over the firing button 5. The contact plate 13 of the trigger locking section 4 is then brought into contact with the area of skin to be pricked, e.g. the pad of a finger on the user's other hand. Pressure is applied to push the contact plate 13 inwardly relative to the body of the lancet device, compressing the platform springs 16a, 16b in the process. A force of at least 1N, more preferably around 6N, must be applied to overcome the resistance of the platform springs 16a,16b. Simultaneously, the user depresses the firing button 5. At some point in the travel of the trigger locking section 4, the trigger release hole 27 will be aligned beneath the trigger stop member 7, allowing the trigger stop member 7 to pass through the hole 27. This will happen quickly, and as the button 5 advances the lancet release member 6 will come into contact with the latch 23. The sloping side surface of the member 6 will push the latch back against the body 20 of the lancet, causing the latch 23 to be released from the lancet catch 10. The spring 31 will then drive the lancet 19 through the casing 1 until the head 29 of the overmolded section on the needle contacts the inner surface of the contact plate, surrounding the opening 14 therein, preventing further progress of the head 29. (In an alternative arrangement, the opening 14 may be large enough to allow passage of the head 29, in which case the user's skin provides the stop surface for the head.)

The spring 31 continues to apply a force to the lancet 19, driving the tip of the needle through the head 29. This results in the a concertina-ing of the sleeve 30 around the needle. The needle tip 21 is driven out through the opening 14 in the contact plate 13, and pierces the skin of the user. At this point, the spring 31 is slightly over extended and begins to contract, pulling the lancet and with it the needle tip back through the opening in the contact plate into the casing.

An important feature of this embodiment is that the overmolded cover 25 covering the lancet needle is of such material and such dimensions that it does not return fully to its original position following firing. Thus, after firing, the tip of the needle remains uncovered. This has two significant advantages. Firstly, and assuming that the needle tip is visible through the casing (the casing may be formed of a transparent plastics material), this provides the user with a visual indication that the device has been fired. Secondly, it prevents the cover 25 from performing a wiping action across the needle tip which might otherwise result in a droplet of blood falling from the tip and giving rise to a contamination/infection risk.

It will be appreciated that, one used, the lancet device cannot be reused, as the spring 31 has been released and it is not possible for a user to recock it. This is prevented by the presence of the trigger locking section 4, and in particular the contact plate which, if depressed by external pressure will move inwardly only to a very limited extent, defined by the position of a contact plate stop ribs formed on the inside surfaces of the upper and lower casing sections.

It will be appreciated by the person of skill in the art that various modifications may be made to the above described embodiments without departing from the scope of the present invention.

The invention claimed is:

1. A skin pricking apparatus comprising a casing, a lancet located within the casing, a spring which is compressed in the non-use state of the apparatus coupled between the lancet and the casing for applying in use a force to drive a needle tip of the lancet through an opening in the casing to prick the skin of a user, and a firing mechanism comprising:
    a finger actuable trigger;
    a trigger locking mechanism moveable between a first position in which the trigger is locked and a second position in which the trigger is unlocked, the trigger locking mechanism comprising a contact plate through which said opening in the casing is formed, the contact plate having an outer contact surface for engaging an area of a user's skin to be pricked, and the contact plate is coupled to the casing by one or more spring means arranged to bias the contact plate outwardly with respect to the casing;
    a latch formed on the lancet or on the inside of the casing which engages a catch formed on the other of the lancet or casing to retain the lancet within the casing with the spring in the compressed state and;
    a lancet release member depending from the trigger to engage the catch or latch when the trigger locking mechanism is in said second position and said trigger is depressed, to release the lancet,
    wherein the trigger locking mechanism and the finger actuable trigger together provide a mechanical interlock which can be released by substantially simultaneous external pressure applied by a user to the trigger locking mechanism and the finger actuable trigger, the mechanical interlock comprising a stop member on the finger actuable trigger arranged to engage a surface of the trigger locking mechanism when the trigger locking mechanism is in said first position, and is arranged to engage a release portion of the surface of the trigger locking mechanism when the trigger locking mechanism is in said second position.

2. Apparatus according to claim 1, wherein said finger actuable trigger and said trigger locking mechanism are molded integrally with said casing.

3. Apparatus according to claim 2, wherein said trigger and said trigger locking mechanism are arranged to be movable in substantially mutually orthogonal directions.

4. Apparatus according claim 2, wherein said trigger locking mechanism is moveable in a direction substantially parallel to the direction of travel of the lancet through the casing.

5. Apparatus according to claim 1, wherein said trigger and said trigger locking mechanism are arranged to be movable in substantially mutually orthogonal directions.

6. Apparatus according to claim 5, wherein said trigger locking mechanism is moveable in a direction substantially parallel to the direction of travel of the lancet through the casing.

7. Apparatus according to claim 1, wherein said trigger locking mechanism is moveable in a direction substantially parallel to the direction of travel of the lancet through the casing.

8. Apparatus according to claim 1, wherein at least one such spring means is attached to the casing by a flexible hinge, whereby during assembly the trigger locking mechanism can be folded inside the casing.

9. Apparatus according to claim 8, the spring means being arranged to provide a resistance to inward movement of the contact plate which is overcome by a force of greater than 1 N.

10. Apparatus according to claim 1, the spring means being arranged to provide a resistance to inward movement of the contact plate which is overcome by a force of greater than 1 N.

11. Apparatus according to claim 1, the release portion of the trigger locking mechanism comprising a passage through the trigger locking mechanism arranged to receive the stop member when the trigger locking mechanism is in said second position.

12. Apparatus according to claim 1, wherein the lancet comprises:
- a body of a substantially rigid plastics material;
- a needle having one end embedded in said body, leaving the other end including a sharpened needle tip to protrude from the body; and
- a flexible plastics cover covering the entire exposed length of the needle, the cover being formed of such material and with such dimensions that an axial force applied to the cover relative to the body causes at least an axial portion of the cover to concertina along the needle, thereby exposing the needle tip.

13. Apparatus according to claim 12, said cover being formed of such material and with such dimensions that it does not recover to cover the needle tip following removal of said axial force.

14. Apparatus according to claim 13, the flexible plastics cover comprising a head portion surrounding the needle tip and a sleeve portion which is narrower than the head portion, surrounding the remainder of the needle, whereby in use said axial force is applied to the head of the cover and the sleeve portion concertinas along the needle in response.

15. Apparatus according to claim 12, said flexible plastics cover being a thermoplastic elastomer material.

16. A method of manufacturing the apparatus of claim 12, the method comprising forming said flexible plastics cover by overmolding a flexible plastics material on top of the needle.

\* \* \* \* \*